United States Patent [19]

Wambach

[11] Patent Number: 4,855,444

[45] Date of Patent: Aug. 8, 1989

[54] α-PYRROLIDONES AND A METHOD FOR PREPARATION THEREOF

[75] Inventor: Ludwig Wambach, Heidelberg, Fed. Rep. of Germany

[73] Assignee: BASF Aktiengesellschaft, Ludwigshafen, Fed. Rep. of Germany

[21] Appl. No.: 177,846

[22] Filed: Mar. 28, 1988

Related U.S. Application Data

[62] Division of Ser. No. 90,451, Aug. 28, 1987, abandoned.

[30] Foreign Application Priority Data

Sep. 16, 1986 [DE] Fed. Rep. of Germany ....... 3631414

[51] Int. Cl.⁴ ............... C07D 201/08; C07D 207/263; C07D 207/267; C07D 207/273
[52] U.S. Cl. .................... 548/408; 548/543; 548/545
[58] Field of Search .......... 548/543, 408, 545

[56] References Cited

U.S. PATENT DOCUMENTS

| | | | |
|---|---|---|---|
| 3,843,781 | 10/1974 | Masuda et al. | 514/423 |
| 3,975,400 | 8/1976 | Himmele et al. | 548/543 |
| 4,208,382 | 6/1980 | Blume et al. | 423/210 |
| 4,460,385 | 7/1984 | Pan et al. | 55/73 |
| 4,484,934 | 11/1984 | Fevrin et al. | 423/228 |

FOREIGN PATENT DOCUMENTS

| | | |
|---|---|---|
| 6724781 | 6/1983 | Australia . |
| 0694043 | 7/1940 | Fed. Rep. of Germany . |
| 0861845 | 5/1953 | Fed. Rep. of Germany . |
| 1795007 | 1/1972 | Fed. Rep. of Germany . |

OTHER PUBLICATIONS

Organic Syntheses, vol. 32, pp. 59–61.

*Primary Examiner*—David B. Springer
*Attorney, Agent, or Firm*—Keil & Weinkauf

[57] ABSTRACT

α-Pyrrolidones and cyclic amidines Ia and Ib, respectively, for washing gases.

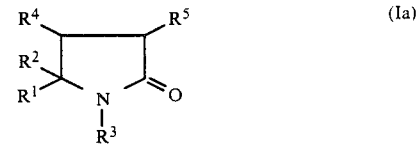

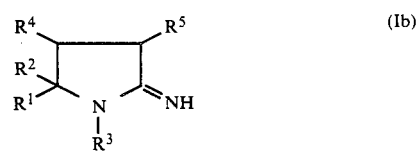

where $R^1$ and $R^2$ are each $C_1$–$C_8$-alkyl, $C_1$–$C_8$-alkoxy, $C_3$–$C_{10}$-cycloalkyl or $C_3$–$C_{10}$-cycloalkoxy or are bonded to one another to form a ring, $R^3$ is hydrogen, $C_1$–$C_6$-alkyl, phenyl or naphthyl and $R^4$ and $R^5$ are each hydrogen or $C_1$–$C_4$-alkyl, are prepared by a method in which an amine II

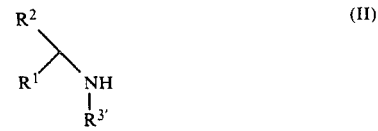

where $R^{3'}$ is hydrogen, tert-butyl, phenyl or naphthyl, is reacted with an α,β-unsaturated carboxylic acid derivative III

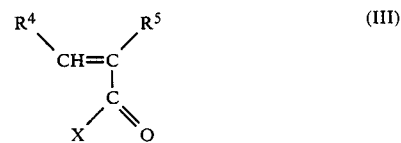

where X is OR', —NR'R", —NHR' or —NH$_2$ and R' and R" are each $C_1$–$C_8$-alkyl, $C_3$–$C_8$-cycloalkyl or phenyl, or with an α,β-unsaturated nitrile IV

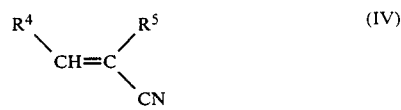

in the presence of a free radical initiator, and, where $R^{3'}$ is hydrogen and it is intended to prepare a compound in which $R^{3'}$ is $C_1$–$C_6$-alkyl, the product obtainable in this procedure is reacted with an alkylating agent to introduce a $C_1$–$C_6$-alkyl group.

7 Claims, No Drawings

α-PYRROLIDONES AND A METHOD FOR PREPARATION THEREOF

This application is a division of application Ser. No. 090,451, filed on Aug. 28, 1987, now abandoned.

The present invention relates to a process for the preparation of α-pyrrolidones and their imines, and the use of the products for washing gases.

It is known that amines very readily undergo a reaction of the Michael addition type with α,β-unsaturated carboxylic acid derivatives or α,β-unsaturated nitriles, open-chain, saturated compounds being formed.

α-Pyrrolidones have been prepared to date by reacting lactones with ammonia or amines (cf. DE-A-1 795 007). This process is relatively expensive since the lactones generally first have to be prepared. Other methods too, for example via the corresponding nitrocarboxylic acids, as described in Org. Synth. 32 (1952), 59, are substantially more expensive (cf. DE-A-861 845).

It is an object of the present invention to provide a novel process for the preparation of α-pyrrolidones and their imines of the general formulae Ia and Ib

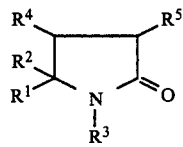

(Ia)

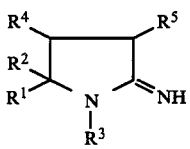

(Ib)

where $R^1$ and $R^2$ are each $C_1$–$C_8$-alkyl, $C_1$–$C_8$-alkoxy, $C_3$–$C_{10}$-cycloalkyl or $C_3$–$C_{10}$-cycloalkoxy and $R^1$ and $R^2$ having together may form a ring having, in particular, from 4 to 7 ring carbon atoms, $R^3$ is hydrogen, $C_1$–$C_6$-alkyl, phenyl or naphthyl and $R^4$ and $R^5$ are each hydrogen or $C_1$–$C_4$-alkyl, which permits the desired compounds to be prepared in a simple and economical manner.

We have found that this object is achieved if an amine of the general formula II

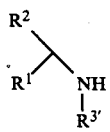

(II)

where $R^{3'}$ is hydrogen, tert-butyl, phenyl or naphthyl, is reacted with an α,β-unsaturated carboxylic acid derivative of the general formula III

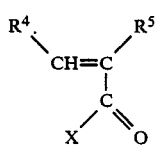

(III)

where X is —OR′, —NR′R″, —NHR′ or —NH$_2$, in which R′ and R″ are each $C_1$–$C_8$-alkyl, $C_3$–$C_8$-cycloalkyl or phenyl, or with an α,β-unsaturated nitrile of the general formula IV

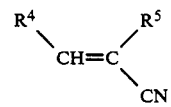

(IV)

in the presence of a free radical initiator, and, where $R^{3'}$ is hydrogen and it is intended to prepare compounds in which $R^3$ is $C_1$–$C_6$-alkyl, the product obtainable in this procedure is reacted with an alkylating agent to introduce a $C_1$–$C_6$-alkyl group.

In a preferred embodiment of the novel process, alkyl peresters, dialkyl peroxides, diaryl peroxides or azo compounds are used as free radical initiators. In general, the free radical initiator used can be any peroxides and azo compounds which are suitable for free radical formation and do not undergo a spontaneous reaction with amines. Azobisisobutyronitrile and 2,2′-azobis-(2,4-dimethylvaleronitrile) are particularly suitable. The use of di-tert-butyl peroxide is also particularly preferred, the process advantageously being carried out at elevated temperatures, for example at about 100°–200° C., in particular 150°–160° C. The choice of the free radical initiator depends in general on the reaction temperature, which is preferably from 50° to 200° C. The reaction temperature is particularly preferably chosen to correspond to the boiling point of the reaction mixture.

In other preferred embodiments, the reaction is carried out under atmospheric or superatmospheric pressure, particularly preferably from 1 to 200 bar. The procedure is advantageously carried out in an autoclave at elevated temperatures under a pressure of, in particular, from 1 to 50 bar.

It is often advantageous to use an excess of amine (II), since this simultaneously serves as a solvent. The ratio of amine (II) to α,β-unsaturated carboxylic acid derivative (III) or the corresponding nitrile (IV) is advantageously from 1:1 to 10:1.

The amount of free radical initiator can be varied within wide limits. For economic reasons, from 5 to 20 mol %, based on the α,β-unsaturated component (III) or (IV), of free radical initiator are advantageous.

The present invention furthermore relates to novel α-pyrrolidones of the general formula Ia′

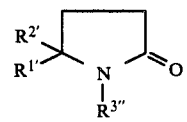

(Ia′)

where $R^{1'}$ and $R^{2'}$ are each $C_1$–$C_4$-alkyl, in particular methyl, or, together with the carbon atom to which they are bonded, may form a ring, in particular a carbocyclic ring, having, in particular, from 4 to 7 ring carbon atoms, and $R^{3''}$ is methyl or tert-butyl.

$R^1$ and $R^2$ are each $C_1$–$C_8$-alkyl, in particular $C_1$–$C_4$-alkyl, especially methyl, ethyl, n-propyl, isopropyl or n-butyl. $R^1$ and $R^2$ may furthermore be $C_1$–$C_8$-alkoxy, in particular $C_1$–$C_4$-alkoxy, for example methoxy, ethoxy or propoxy, $C_3$–$C_{10}$-cycloalkyl, in particular $C_3$–$C_6$-cycloalkyl, e.g. cyclopropyl, cyclobutyl, cyclopentyl or cyclohexyl, or $C_3$–$C_{10}$-cycloalkoxy, in particular $C_3$–$C_6$-cycloalkoxy. The stated groups can, if desired, be further substituted, for example by $C_1$–$C_4$-alkyl, halogen or $C_1$–$C_4$-alkoxy.

$R^3$ is hydrogen or $C_1$–$C_6$-alkyl, phenyl or naphthyl.

$R^4$ and $R^5$ may be hydrogen or $C_1$–$C_4$-alkyl, for example methyl, ethyl, n-propyl, isopropyl or butyl.

In the compounds (III), X may be —OR', —NR'R", —NHR' or —NH$_2$, in which R' and R" are each $C_1$–$C_8$-alkyl, in particular $C_1$–$C_4$-alkyl, $C_3$–$C_8$-cycloalkyl, in particular $C_3$–$C_6$-cycloalkyl, or phenyl. Where X is —NR'R", NHR or NH$_2$, it may be necessary to supply a greater amount or heat in order to obtain the corresponding α-pyrrolidone immediately.

Particularly suitable amines (II) are isopropylamine, cyclohexylamine, cyclopentylamine, sec-butylamine, N-isopropyl-tert-butylamine and N-isopropylaniline. If it is intended to prepare compounds I in which $R^3 \neq R^3{}'$, a radical of this type should be prepared by subsequent alkylation of a compound I in which $R^3$ is H, for example by reaction with an appropriate alkanol or alkyl bromide in a conventional manner.

Particularly preferred α,β-unsaturated carboxylic acid derivatives (III) and (IV) are acrylates, crotonates, acrylamides and acrylonitriles.

In a particularly preferred embodiment, isopropylamine is reacted with methyl acrylate in the presence of di-tert-butyl peroxide to give 5,5-dimethylpyrrolid-2-one.

The novel process is advantageously carried out as follows: the major amount of the amine is initially taken and heated to the desired temperature. The free radical initiator is diluted with the remaining amount of amine, and this solution is metered in simultaneously with the α,β-unsaturated component. Free radical initiators which do not react with the α,β-unsaturated component at room temperature may furthermore be mixed with the said component and metered in.

The compounds Ia and Ib can readily be isolated from the reaction mixture by a conventional separation method, preferably by distillation. If, in the case of the compounds Ib, working up is carried out in the presence of water, the corresponding pyrrolidones Ia are obtained.

The α-pyrrolidones and their imines Ia and Ib are useful intermediates, particularly for pharmaceutical purposes. N-Alkylation of the N-unsubstituted pyrrolidones Ia with $C_1$–$C_6$-alkanols, for example using the procedure according to DE-A-830 194, gives the N-alkylpyrrolidones Ia, which can be used as solvents, for example for washing gases. Among N-alkylpyrrolidones of this type, N-methyl-5,5-dimethylpyrrolid-2-one is a particularly useful solvent for washing gases to remove acidic gases, such as carbon dioxide or hydrogen sulfide from gas mixtures. In this repsect, the compounds according to the invention have the advantage of being insensitive to oxidation, ie. they can be used particularly successfully for washing oxygen-containing gases.

EXAMPLE 1

575 g (9.7 moles) of isopropylamine were initially taken in a 2.5 l autoclave. 300 g (3.5 moles) of methyl acrylate and 15 g (0.1 mole) of di-tert-butyl peroxide, dissolved in 215 g (3.65 moles) of isopropylamine, were then metered in at 150° C. in the course of 2 hours. Stirring was continued for 2 hours. Working up by distillation gave 5,5-dimethylpyrrolid-2-one (boiling point: 85°–87° C./0.5 mbar) in 80% yield.

EXAMPLE 2

7.8 moles of cyclohexylamine and 30 g (0.2 mole) of di-tert-butyl peroxide in 260 g (2.6 moles) of cyclohexylamine were reacted to give 5-spiro-cyclohexylpyrrolid-2-one using a method similar to that described in Example 1. Yield: 70%; melting point: 132°–133° C.; boiling point: 155°–158° C./0.5 mbar.

EXAMPLE 3

3 moles of methyl acrylate and 37 g (0.1 mole) of dry dilauroyl peroxide were gradually added to 8 moles of cyclohexylamine at 80° C., after which stirring was continued for 3 hours at 80° C. Working up by distillation gave 5-spiro-cyclohexylpyrrolid-2-one in 70% yield.

EXAMPLE 4

4,5,5-Trimethylpyrrolid-2-one (boiling point: 98°–100° C./0.3 mbar) was prepared in 30% yield similarly to Example 1, but using 300 g (3 moles) of methyl crotonate instead of the methyl acrylate.

EXAMPLE 5

4,5,5-Trimethylpyrrolid-2-one was obtained in 45% yield by a method similar to that described in Example 4, but using 57.3 g (0.2 mole) of 2,5-dimethyl-2,5-di-tert-butylperoxyhex-3-ine as the free radical initiator and a reaction temperature of 160° C.

EXAMPLE 6

3,5,5-Trimethylpyrrolid-2-one (boiling point: 103°–107° C./0.3 mbar) was prepared in 15% yield similarly to Example 1, but using 342.5 g (3.0 moles) of ethyl methacrylate instead of the methyl acrylate.

EXAMPLE 7

354.7 g (6 moles) of isopropylamine were initially taken, and 213.24 g (3 moles) of acrylamide, dissolved in 213 g of methanol, and 43.87 g (0.3 mole) of di-tert-butyl peroxide, dissolved in 177.35 g (3 moles) of isopropylamine, were added at 150° C. in the course of 2 hours. Stirring was continued for 2 hours. Subsequent working up by distillation gave 5,5-dimethylpyrrolid-2-one in 50% yield.

EXAMPLE 8

575 g (9.7 moles) of isopropylamine were reacted with 189 g (3.5 moles) of acrylonitrile similarly to Example 1, 5,5-dimethylpyrrolidon-2-imine being formed in about 70% yield, according to gas chromatographic analysis.

EXAMPLE 9

A solution of 113 g (1 mole) of 5,5-dimethylpyrrolid-2-one and 96 g (3 moles) of methanol was vaporized, and passed over an alumina catalyst at 400° C. Working up the gas mixture in a conventional manner to obtain 1,5,5-trimethylpyrrolid-2-one gives this compound in about 86% yield; boiling point: 236°–238° C.

I claim:

1. A process for the preparation of an α-pyrrolidone of the formula Ia

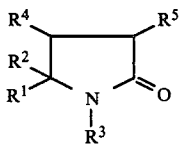

where $R^1$ and $R^2$ are each $C_1$-$C_8$-alkyl, $C_1$-$C_8$-alkoxy, $C_3$-$C_{10}$-cycloalkyl or $C_3$-$C_{10}$-cycloalkoxy and $R^1$ and $R^2$ together may form a ring having, in particular, from 4 to 7 ring carbon atoms, $R^3$ is hydrogen, $C_1$-$C_6$-alkyl, phenyl or naphthyl and $R^4$ and $R^5$ are each hydrogen or $C_1$-$C_4$-alkyl, wherein an amine of the formula II

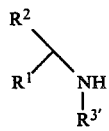

where $R^{3'}$ is hydrogen, tert-butyl, phenyl or naphthyl, is reacted in the presence of a free radical initiator with an α,β-unsaturated carboxylic acid derivative of the formula III

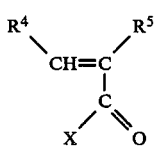

where X is —OR', —NR'R", —NHR' or —NH$_2$, in which R' and R" are each $C_1$-$C_8$-alkyl, $C_3$-$C_8$-cycloalkyl or phenyl, and, where $R^{3'}$ is hydrogen and it is intended to prepare a compound in which $R^3$ is $C_1$-$C_6$-alkyl, the product obtainable in this procedure is reacted with an alkylating agent to introduce a $C_1$-$C_6$-alkyl group.

2. A process as defined in claim 1, wherein the free radical initiator used is an alkyl perester, a dialkyl peroxide, a diaryl peroxide or an azo compound.

3. A process as defined in claim 1, wherein the reaction of (II) with (III) is carried out at from 50° to 200° C.

4. A process as defined in claim 1, wherein the reaction of (II) with (III) is carried out under from 1 to 200 bar.

5. A process as defined in claim 1, wherein the reaction of (II) with (III) is carried out in the presence of an excess of the amine II as a solvent.

6. A α-pyrrolidone of the formula Ia'

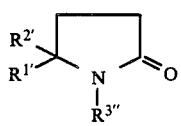

where $R^{1'}$ and $R^{2'}$ are each $C_1$-$C_4$-alkyl or, together with the carbon atom to which they are bonded, may form a ring having, in particular, from 4 to 7 ring carbon atoms, and $R^{3''}$ is methyl or tert-butyl.

7. An α-pyrrolidone of the formula Ia' as defined in claim 6, wherein $R^{1'}$, $R^{2'}$, $R^{3'}$ are each methyl.

* * * * *